United States Patent
Boehm

(10) Patent No.: US 10,825,155 B2
(45) Date of Patent: Nov. 3, 2020

(54) PROVIDING A NORMALIZED IMAGE

(71) Applicant: Siemens Healthcare GmbH, Erlangen (DE)

(72) Inventor: Stefan Boehm, Oberasbach (DE)

(73) Assignee: Siemens Healthcare GmbH, Erlangen (DE)

( * ) Notice: Subject to any disclaimer, the term of this patent is extended or adjusted under 35 U.S.C. 154(b) by 209 days.

(21) Appl. No.: 15/993,696

(22) Filed: May 31, 2018

(65) Prior Publication Data
US 2018/0350051 A1 Dec. 6, 2018

(30) Foreign Application Priority Data
Jun. 6, 2017 (EP) .................................... 17174564

(51) Int. Cl.
*G06T 5/50* (2006.01)
*A61B 6/00* (2006.01)
(Continued)

(52) U.S. Cl.
CPC ................ *G06T 5/50* (2013.01); *A61B 6/582* (2013.01); *G06T 5/009* (2013.01); *G06T 5/40* (2013.01);
(Continued)

(58) Field of Classification Search
CPC .. G06T 5/009; G06T 5/40; G06T 5/50; G06T 2207/10116; G06T 2207/30101; G16H 30/20; G16H 30/40; A61B 6/582
(Continued)

(56) References Cited

U.S. PATENT DOCUMENTS

| | | | |
|---|---|---|---|
| 8,553,963 B2* | 10/2013 | Rauch | G06T 7/20 378/21 |
| 8,805,041 B2* | 8/2014 | Miyamoto | G06T 5/009 382/130 |
| 2010/0166276 A1 | 7/2010 | Dube | |

OTHER PUBLICATIONS

Rosas-Romero, Roberto et al: "A method to assist in the diagnosis of early diabetic retinopathy: Image processing applied to detection of microaneurysms in fundus images"; in: Computerized Medical Imaging and Graphics; vol. 44; pp. 41-53; 2015; XP0554.14304, US; ISSN: 0895-6111; DOI: 10.1016/j.compmedimag.2015.07.001.
(Continued)

*Primary Examiner* — Daniel G Mariam
(74) *Attorney, Agent, or Firm* — Harness, Dickey & Pierce, P.L.C.

(57) ABSTRACT

A method is for providing a normalized image. The method includes receiving a non-normalized image including first pixels and non-normalized intensities, each of the first pixels being characterized by one of the non-normalized intensities. Furthermore, the method includes determining a subtraction histogram, the subtraction histogram being configured to map a first intensity to the difference between the relative frequency of the first intensity and the relative frequency of a second intensity, the first intensity being one of the non-normalized intensities and the second intensity being one of the non-normalized intensities. Furthermore, the method includes providing a normalized image including second pixels and normalized intensities based on the non-normalized image and based on the subtraction histogram, each of the second pixels being characterized by one of the normalized intensities.

24 Claims, 6 Drawing Sheets

(51) Int. Cl.
     *G16H 30/20*     (2018.01)
     *G06T 5/40*      (2006.01)
     *G06T 5/00*      (2006.01)

(52) U.S. Cl.
     CPC .... *G16H 30/20* (2018.01); *G06T 2207/10116* (2013.01); *G06T 2207/30101* (2013.01)

(58) Field of Classification Search
     USPC ........................................................ 382/168
     See application file for complete search history.

(56)                References Cited

OTHER PUBLICATIONS

Extended European Search Report #17174564.9 dated Oct. 19. 2017.

\* cited by examiner

PROVIDING A NORMALIZED IMAGE

PRIORITY STATEMENT

The present application hereby claims priority under 35 U.S.C. § 119 to European patent application number EP17174564.9 filed Jun. 6, 2017, the entire contents of which are hereby incorporated herein by reference.

FIELD

At least one embodiment of the invention generally relates to a method for providing a normalized image.

BACKGROUND

Imaging of vessels in an examination region, e.g. blood vessels in a patient, using X-ray imaging (the technical term is "angiography") is difficult due to the low X-ray attenuation of the vessels and/or of the contents of the vessels.

A common solution to this problem is to use subtraction angiography, where two images of the examination region are recorded, wherein the vessel contains no contrast fluid in the first image and contains contrast fluid in the second image, wherein the contrast fluid has high X-ray attenuation. Each of the images comprises image intensities, in particular X-ray intensities. A difference between the first image and the second image can then be used as a subtraction image, which enhances changes of the image intensities between the two images, and which in an optimal case (without noise and without motion artifacts) would only display the contribution of the contrast fluid. Additionally in this setup, subtraction angiography can be used to quantify the fluid flow within the vessel.

A common technique for subtraction angiography is "digital subtraction angiography" (a short term is "DSA"), wherein the first image and the second image are recorded using a pixelated X-ray detector, e.g. a flat panel X-ray detector. Such a X-ray detector and an X-ray source can be mounted e.g. on a C-arm X-ray imaging device to allow taking X-ray images from different view angles during an intervention. Within DSA the subtraction image can be calculated pixel-by-pixel.

Angiography imaging can be used during interventions ("interventional angiography"), e.g. within the roadmap method, wherein a subtracted vessel image and a fluoroscopic live image containing small surgical devices are overlaid, in order to use the subtracted vessel image for navigation.

The vessels displayed in the subtracted vessel map are exposed to volatile external effects, e.g. the concentration of radiopaque material, the patient's anatomy and the filling phase (which can be arterial or venous), which lead to different image contrasts. Such variations of the image contrast can lead wrong choices in diagnosis or therapy in general, or to navigational errors in using the roadmap method.

It is known to use a statistical analysis of the subtracted image in order to reduce the variation in the image contrast. These analysis are limited especially if motion artifacts between the first and the second image are present.

SUMMARY

At least one embodiment of the present invention provides an image with reduced variations of the image contrast, even if motion artifacts are present.

Embodiments of the present invention are directed to a method; a providing apparatus; an X-ray imaging apparatus; a computer program product; and a computer-readable storage medium.

Embodiments according to the invention are described with respect to apparatuses as well as with respect to the methods. Features, advantages or alternative embodiments herein can be assigned to the other claimed objects and vice versa. In other words, claims for the apparatus can be improved with features described or claimed in the context of the method. In this case, the functional features of the method are embodied by objective units of the apparatus.

At least one embodiment of the invention relates to a method for providing a normalized image, wherein in particular the method is implemented by one or more computing devices. The method comprises receiving a non-normalized image comprising first pixels and non-normalized intensities by an interface, wherein each of the first pixels is characterized by one of the non-normalized intensities. Furthermore, the method comprises determining a subtraction histogram with a calculation unit, wherein the subtraction histogram maps a first intensity to the difference between the relative frequency of the first intensity and the relative frequency of a second intensity, wherein the first intensity is one of the non-normalized intensities and the second intensity is one of the non-normalized intensities. Furthermore, the method comprises providing (PROV) a normalized image comprising second pixels and normalized intensities based on the non-normalized image and based on the subtraction histogram with the calculation unit, wherein each of the second pixels is characterized by one of the normalized intensities.

At least one embodiment of the invention relates to a providing apparatus for providing a normalized image, comprising the following units:
  interface, configured for receiving a non-normalized image comprising first pixels and non-normalized intensities by an interface, wherein each of the first pixels is characterized by one of the non-normalized intensities,
  calculation unit, configured for determining a subtraction histogram, wherein the subtraction histogram maps a first intensity to the difference between the relative frequency of the first intensity and the relative frequency of a second intensity, wherein the first intensity is one of the non-normalized intensities and the second intensity is one of the non-normalized intensities,
furthermore configured for providing a normalized image comprising second pixels and normalized intensities based on the non-normalized image and based on the subtraction histogram, wherein each of the second pixels is characterized by one of the normalized intensities.

At least one embodiment of the invention relates to an X-ray imaging device, comprising a providing apparatus according to an embodiment of the invention.

At least one embodiment of the invention relates to an X-ray imaging device comprising an X-ray source and an X-ray detector, and configured for recording X-ray images of an examination volume, in particular X-ray projections. The X-ray imaging device can be realized as a C-arm X-ray imaging device.

At least one embodiment of the invention relates to a computer program product comprising a computer program, the computer program being loadable into a memory unit of a providing apparatus, including program code sections to make the providing apparatus execute the method according to an embodiment of the invention when the computer program is executed in said providing apparatus.

At least one embodiment of the invention relates to a computer-readable medium, on which program code sections of a computer program are saved, said program code sections being loadable into and/or executable in a providing apparatus to make the providing apparatus execute the method according to an embodiment of the invention when the program code sections are executed in providing apparatus.

DETAILED DESCRIPTION OF THE EXAMPLE EMBODIMENTS

Figure 1:
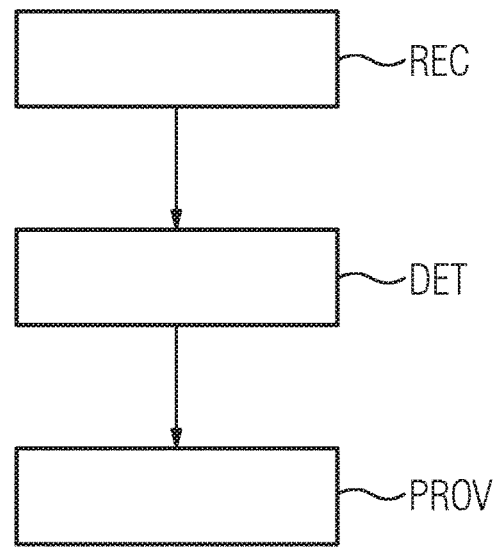
FIG. 1 shows a flow chart of a first embodiment of the method for providing a normalized image.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for providing a normalized image, wherein in particular the method is implemented by one or more computing devices. The method comprises receiving a non-normalized image comprising first pixels and non-normalized intensities by an interface, wherein each of the first pixels is characterized by one of the non-normalized intensities. Furthermore, the method comprises determining a subtraction histogram with a calculation unit, wherein the subtraction histogram maps a first intensity to the difference between the relative frequency of the first intensity and the relative frequency of a second intensity, wherein the first intensity is one of the non-normalized intensities and the second intensity is one of the non-normalized intensities. Furthermore, the method comprises providing (PROV) a normalized image comprising second pixels and normalized intensities based on the non-normalized image and based on the subtraction histogram with the calculation unit, wherein each of the second pixels is characterized by one of the normalized intensities.

The relative frequency of the first intensity is the relative frequency of the first intensity with respect to the non-normalized intensities. The relative frequency of the second intensity is the relative frequency of the second intensity with respect to the non-normalized intensities.

The inventor has recognized that based on such a histogram normalized intensities can be calculated particularly fast and efficient, while at the same time the influence of motion artifacts can be taken into account.

According to a further embodiment of the invention, the relative deviation between the negative of the first intensity and the second intensity is smaller than 0.5, or in particular smaller than 0.1, or in particular smaller than 0.05, or in particular smaller than 0.01. The negative of the first intensity is the first intensity multiplied by (−1). The relative deviation 51 between the negative $-I_1$ of the first intensity $I_1$ and the second intensity $I_2$ is defined as $\delta I = |(-I_1 - I_2)/I_1|$. The inventor has recognized that this choice of the second intensity leads to a high fineness of the motion artifact correction for the normalized intensities.

According to a further embodiment of the invention, the second intensity is the negative of the first intensity. The inventor has recognized that this choice of the second intensity leads to a high fineness of the motion artifact correction for the intensities especially in situations of small motions.

According to a further embodiment of the invention, the subtraction histogram maps the first intensity to zero if the first intensity is positive. The inventors have recognized that especially in medical subtraction imaging (e.g. in digital subtraction angiography) the relevant intensities are the negative intensities, because they correspond to contrast fluid (where vessels with contrast fluid have a higher X-ray absorption rate than vessels without contrast fluid). So a restriction of the subtraction histogram to negative values is a restriction to the medical relevant part of the histogram.

According to a further embodiment of the invention, each of the second pixels is assigned to one of the first pixels, wherein the normalized intensities pixel-wisely depend on the non-normalized intensities. In other words, the normalized intensity of one of the second pixels does not depend on the non-normalized intensity of one of the first pixels, if the said second pixel is not assigned to the said first pixels. In other words, the only one of the non-normalized intensities a normalized intensity of one of the second pixels depends on is the non-normalized intensity of the one of the first pixels the second pixel is assigned to. Herein the term "does not depend" does not exclude an indirect dependence, e.g. a dependence on the measured mean or the measured deviation. The inventor has recognized that a pixel-wise normalization is in particular fast and efficient.

According to a further embodiment of the invention, the normalized intensity of one of the second pixels is a linear function of the non-normalized intensity of the one of the first pixels, wherein the said one of the second pixels is assigned to the said one of the first pixels. The inventor has recognized that the usage of a linear function leads to a fast and efficient computation of the normalized intensities.

According to a further embodiment of the invention, the step of providing is based on a measured mean and a measured deviation, wherein the measured mean is the mean of the non-normalized intensities weighted according to the subtraction histogram, and wherein the measured deviation is the standard deviation of the non-normalized intensities weighted according to the subtraction histogram. In other words, the measured mean is the mean of the non-normalized intensities weighted according to the subtraction histogram, and the measured deviation is the standard deviation of the non-normalized intensities weighted according to the subtraction histogram. The inventor has recognized that the measured mean and the measured deviation within the subtraction histogram are especially suited for characterizing the intensity distribution fast and efficient.

The measured mean $\mu_m$ is in particular defined as $$\mu_m := \int x \cdot H_s(x) dx$$

wherein the integral is calculated over the non-normalized intensities x, and $H_s(x)$ denotes the value the subtraction histogram $H_s$ maps the non-normalized intensity x onto. The measured deviation $\sigma_m$ is in particular defined as $$\sigma_m := \sqrt{\int (x-\mu m)^2 H_s(s) dx}.$$

According to a further embodiment of the invention, within the step of receiving furthermore a reference mean and a reference deviation are received, and wherein the step of providing is furthermore based on the reference mean and the reference deviation. The inventor has recognized that the reference mean and the reference deviation can be used together with the measured mean and the measured deviation to bring the distribution of the intensities in the subtraction histogram to a standard form given by the measured mean and the measured deviation fast and efficient.

According to a further embodiment of the invention, each of the second pixels is assigned to one of the first pixels, wherein a normalized intensity of one of the second pixels is calculated as the sum of two numbers, wherein the first number is the product of a first constant with the non-normalized intensity value of the one of the first pixels assigned to the one of the second pixels, wherein the second number is a second constant, wherein the first constant is the ratio of the reference deviation and the measured deviation, and wherein the second constant is the reference mean subtracted by the product of the first constant and the measured mean. The inventor has recognized that this linear transformation can be used for mapping the non-normalized intensities to normalized intensities in a fast and efficient way, while at the same time the measured mean and the measured deviation are being transformed to the reference mean and the reference deviation.

According to a further embodiment of the invention, the step of determining the subtraction histogram comprises a first substep of determining an initial histogram with the calculation unit, wherein the initial histogram maps the first intensity to the relative frequency of the first intensities, and a second substep of determining the subtraction histogram based on the initial histogram with the calculation unit. The inventor has recognized that by determining the initial histogram before the subtraction histogram properties of the initial histogram can be used for the determining of the subtraction histogram or for the providing of the normalized image more precisely.

According to a possible further embodiment of the invention, the relative frequency of the first intensity is the number of occurrences of the first intensity in the non-normalized intensities divided by the total number of non-normalized intensities. The inventor has recognized that using the number of occurrences of a single intensity as the relative frequency leads to a more exact calculation of a normalized image.

According to a possible further embodiment of the invention, the relative frequency of the first intensity is the number of occurrences of an interval of intensities in the non-normalized intensities divided by the total number of non-normalized intensities, wherein the interval of intensities contains the first intensity. The inventor has recognized that using the number of occurrences of a subset of intensities leads to a fast calculation of the normalized image.

At least one embodiment of the invention relates to a providing apparatus for providing a normalized image, comprising the following units:

interface, configured for receiving a non-normalized image comprising first pixels and non-normalized intensities by an interface, wherein each of the first pixels is characterized by one of the non-normalized intensities, calculation unit, configured for determining a subtraction histogram, wherein the subtraction histogram maps a first intensity to the difference between the relative frequency of the first intensity and the relative frequency of a second intensity, wherein the first intensity is one of the non-normalized intensities and the second intensity is one of the non-normalized intensities, furthermore configured for providing a normalized image comprising second pixels and normalized intensities based on the non-normalized image and based on the subtraction histogram, wherein each of the second pixels is characterized by one of the normalized intensities.

In particular the providing apparatus can be embodied to execute the method according to the invention and its embodiments. The providing apparatus is embodied to execute the method, in its embodiments, by the interface and the calculation unit being embodied to execute the respective method steps.

The providing apparatus can be realized as a data processing system or as a part of a data processing system. The providing apparatus can, for example, comprise a cloud-computing system, a computer network, a computer, a tablet computer, a smartphone or the like. The providing apparatus can comprise hardware and/or software. The hardware can be, for example, a processor system, a memory system and combinations thereof. The hardware can be configurable by the software and/or be operable by the software.

At least one embodiment of the invention relates to an X-ray imaging device, comprising a providing apparatus according to an embodiment of the invention.

At least one embodiment of the invention relates to an X-ray imaging device comprising an X-ray source and an X-ray detector, and configured for recording X-ray images of an examination volume, in particular X-ray projections. The X-ray imaging device can be realized as a C-arm X-ray imaging device.

At least one embodiment of the invention relates to a computer program product comprising a computer program, the computer program being loadable into a memory unit of a providing apparatus, including program code sections to make the providing apparatus execute the method according to an embodiment of the invention when the computer program is executed in said providing apparatus.

At least one embodiment of the invention relates to a computer-readable medium, on which program code sections of a computer program are saved, said program code sections being loadable into and/or executable in a providing apparatus to make the providing apparatus execute the method according to an embodiment of the invention when the program code sections are executed in providing apparatus.

The realization of at least one embodiment of the invention by a computer program product and/or a computer-readable medium has the advantage that already existing providing apparatuses can be easily adopted by software updates in order to work as proposed by at least one embodiment of the invention.

The computer program product can be, for example, a computer program or comprise another element apart from the computer program. This other element can be hardware, for example a memory device, on which the computer program is stored, a hardware key for using the computer program and the like, and/or software, for example a documentation or a software key for using the computer program.

A non-normalized image and/or a normalized image can in particular be a subtraction image, or a difference between a first and a second image. The first image and/or the second image can be X-ray projections of an examination volume. In particular a non-normalized image and/or a normalized image can be a digital subtraction angiography image (abbreviated by "DSA-image") which is generated by calculating the difference between a first image of the examination volume with contrast fluid and a second image of the examination volume without contrast fluid. In order to have only small motion artifacts, the time interval between the recordings of the first and the second image has to be chosen small (in particular below ten minutes, in particular below 1 minute, in particular below 10 seconds) and/or the examination volume must not be moved between the recordings of the first and the second image.

A first intensity and/or a second intensity can take positive and negative values, and the value zero. If the non-normalized and/or the normalized image are a subtraction image, in particular a difference between a first and a second image, an first intensity and/or a second intensity of the non-normalized image and/or the normalized image can be defined as the difference between an intensity of the first image and an intensity of the second image. In particular, the first intensity and/or a second intensity of the non-normalized image and/or the normalized image can be defined as the difference between an intensity of a pixel of the first image and an intensity of a corresponding pixel of the second image.

A pixel of the first pixels and/or the second pixels can refer to an elementary two-dimensional building block of a two-dimensional image, especially of a spatial two-dimensional image. A pixel can also refer to a higher-dimensional building block of a higher-dimensional image, especially a spatial higher-dimensional image. In particular, a pixel can refer to a voxel, and/or a pixel can contain additional time information, wherein the time information is inherited by the image the pixel is contained in. Each pixel of the first pixels is characterized by a non-normalized intensity, and each pixel of the second pixels is characterized by a normalized intensity.

The number of the second pixels can be equal to the number of first pixels. Additionally the arrangement of the second pixels can be equal to the arrangement of the first pixels, so that there is a one-to-one correspondence between the first pixels and the second pixels. In a one-to-one correspondence each of the second pixels can be assigned to one of the first pixels. In particular, the first pixels and the second pixels can both be arranged in a rectangle including same edge lengths; alternatively the first pixels and the second pixels can both be arranged in a cubus including same edge lengths.

FIG. 1 shows a flow chart of a first embodiment of the method for providing a normalized image. The first step of this embodiment is receiving REC a non-normalized image 430, 530 comprising first pixels and non-normalized intensities 601 by an interface 301, wherein each of the first pixels is characterized by one of the non-normalized intensities 601.

The non-normalized image 430, 530 in this embodiment is the difference between a first image 410, 510 and a second image 420, 520, wherein the first image 410, 510 and the second image 420, 520 comprise the same number of pixels, and wherein the arrangement of the pixels of the first image 410, 510 is equals the arrangement of the pixels of the second image 420, 520, so that there is a one-to-one correspondence between pixels of the first image 410, 510 and the pixels of the second image 420, 520.

In this embodiment, the non-normalized intensities 601 are relative intensities. Each of the non-normalized intensities 601 is the difference between the intensity of one of the pixels of the first image 410, 510 and the intensity of the corresponding one of the pixels of the second image 420, 520. As a consequence, non-normalized intensities 601 can be negative, zero or positive.

This embodiment can be used for the non-normalized image 430, 530 being a digital subtraction angiography image. In this case the first image and the second image are images of the same region of interest, wherein the region of interest contains a vessel, and wherein during the recording of the second image there is more contrast fluid in the vessel that during the recording of the first image. The intensities of the non-normalized image 430, 530 are then calculated as $$I_{NN}(x,y)=I_2(x,y)-I_1(x,y)$$

wherein $I_{NN}(x,y)$ is the intensity of the pixel including the coordinates x and y in the non-normalized image, and wherein $I_1(x,y)$ and $I_2(x,y)$ are the intensities of the pixel characterized by the coordinates x and y in the first and the second image.

The next step of this embodiment is determining DET a subtraction histogram 800 with the calculation unit 302, wherein the subtraction histogram 800 maps a first intensity to the difference between the relative frequency 602 of the first intensity and the relative frequency 602 of a second intensity, wherein the first intensity is one of the non-normalized intensities 601 and the second intensity is one of the non-normalized intensities 601. Here the relative frequency 602 of a first intensity and a second intensity is a measure for the relative frequency 602 of the first intensity and the second intensity within the non-normalize intensities.

In this embodiment, the relative frequency 602 of a first intensity and a second intensity is the relative frequency 602 of the first intensity and the second intensity within the non-normalized intensities 601, which is the number of occurrences of the first intensity and the second intensity in the non-normalized intensities 601 divided by the total number of non-normalized intensities 601.

Alternatively, each of the relative frequency 602 of a first intensity and a second intensity can also be the relative frequency 602 of a subset of intensities containing the first intensity and the second intensity, or in particular of an interval of non-normalized intensities 601 containing the first intensity and the second intensity. A technical term for this definition is binning. The boundaries of the intervals can be defined independently of the first frequency (e.g. by the intervals [k·ΔI, (k+1)·ΔI[, where k is an integer number and ΔI is the width of the interval). Alternatively, the boundaries can also be defined relative to the first intensity (e.g. by [x−ΔI/2, x−ΔI/2], where x is the first intensity and ΔI is the width of the interval.

Alternatively, each of the relative frequencies of a first intensity and a second intensity can also be calculated using a kernel density estimation.

$$H(i) = \frac{1}{nh}\sum_{x,y} K\left(\frac{i-I_{NN}(x,y)}{h}\right)$$

wherein n is the number of non-normalized intensities 601, h>0 is a smoothing parameter, and K is the kernel function. As a kernel function, one can use for example a Gaussian kernel or a Cauchy kernel. A Gaussian kernel or a Cauchy kernel are given by the formulas $$K_{Gaussian}(i) = \frac{1}{\sqrt{2\pi}}\exp\left(-\frac{i^2}{2}\right); K_{Cauchy}(i) = \frac{1}{\pi(1+i^2)}$$

The smoothing parameter can be chosen arbitrarily, common choices are $$h = \sigma\sqrt[5]{n} \text{ or } h = \sqrt[5]{4\sigma^5/3n},$$

where σ is the standard deviation of the non-normalized intensities 601.

In this embodiment, the second intensity is the negative of the first intensity, so that the subtraction histogram 800 is calculated by $$H_s(x)=H(x)-H(-x)$$

wherein $H_s$ denotes the subtraction histogram 800. Alternatively, the second intensity is the negative of the first intensity up to a constant offset, so that the subtraction histogram 800 is calculated by $$H_s(x)=H(x)-H(c-x)$$

where c is the constant. In particular, the constant can be chosen as the mean of the non-normalized intensities 601, or alternatively as the mean of the non-normalized intensities 601 weighted by their relative frequency 602.

The last step of this embodiment is providing (PROV) a normalized image comprising second pixels and normalized intensities 801 based on the non-normalized image 430, 530 and based on the subtraction histogram 800 with the calculation unit 302, wherein each of the second pixels is characterized by one of the normalized intensities 801.

In this embodiment, the normalized intensity $I_N(x,y)$ of one of the second pixels of the normalized image characterized by the coordinates x and y is a linear function of the non-normalized intensity $I_{NN}(x,y)$ of the corresponding one of the first pixels of the non-normalized image $$I_N(x,y)=m \cdot I_{NN}(x,y)+t$$

where m and t are constants.

In this embodiment, the constants m and t only depend on the measured mean $\mu_m$ and the measured deviation $\sigma_m$ of the non-normalized intensities 601 weighted according to the subtraction histogram 800, and a reference mean 802 $\mu_r$ and a reference $\sigma_r$ deviation. Herein, the measured mean $\mu_m$ and the measured deviation $\sigma_m$ are calculated as $$m = \frac{\sigma_r}{\sigma_m}; t = \mu_r - \mu_m \cdot \frac{\sigma_r}{\sigma_m}$$

The constants m and t can be chosen such that the normalized intensities 801 have a mean equivalent to the reference mean 802 and a standard deviation equivalent to the reference deviation 803 by choosing the constants m and t as $$\mu_m = \int_{-\infty}^{0} x \cdot H_s(x)dx; \sigma_m = \left(\int_{-\infty}^{0}(x-\mu_m)^2 H_s(x)dx\right)^{\frac{1}{2}}.$$

Figure 2:
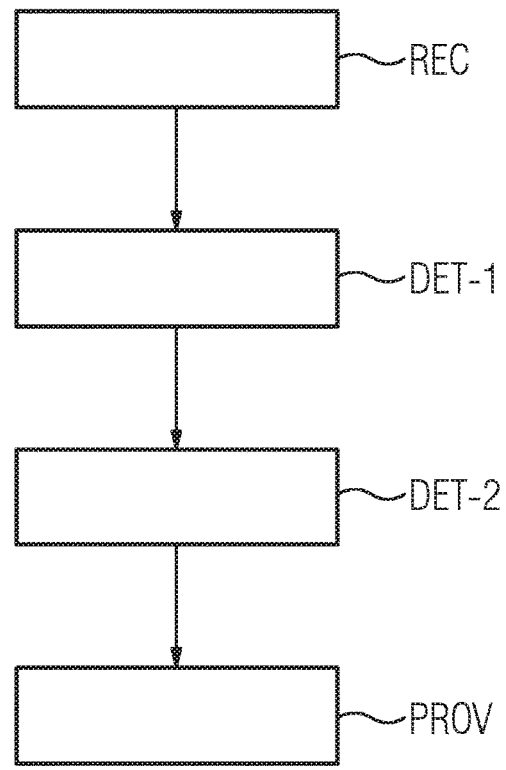
FIG. 2 shows a flow chart of a second embodiment of the method for providing a normalized image.

FIG. 2 shows another embodiment of the method for providing a normalized image. The steps of receiving REC and providing PROV are analogous to the embodiment described in FIG. 1.

Within this embodiment, the step of determining DET is divided in a first substep of determining DET-1 and a second substep of determining DET-2.

In the first substep of determining DET-1 a plain histogram 600 is calculated based on the non-normalized intensities 601 of the non-normalized image 430, 530. The plain histogram 600 maps the first intensity to the relative frequency 602 of the first intensity in the non-normalized intensities 601. Here the relative frequency 602 is a measure for the relative frequency 602 of the first intensity within the non-normalized intensities 601, which is described in detail in the description of FIG. 1.

In the second substep of determining DET-2 the subtraction histogram 800 is calculated based on the plain histogram 600 with the calculation unit 302. In this embodiment, the subtraction histogram 800 is calculated by the following difference of the plain histogram 600 $H_p$ $$H_s(x)=H_p(x)-H_p(-x)$$

wherein $H_s$ denotes the subtraction histogram 800. Alternatively, the the subtraction histogram 800 is calculated by the following difference of the plain histogram 600 $H_p$ $$H_s(x)=H_p(x)-H_p(c-x)$$

where c is a constant. In particular, the constant can be chosen as the mean of the non-normalized intensities 601, or alternatively as the mean of the non-normalized intensities 601 weighted by their relative frequency 602.

Figure 3:
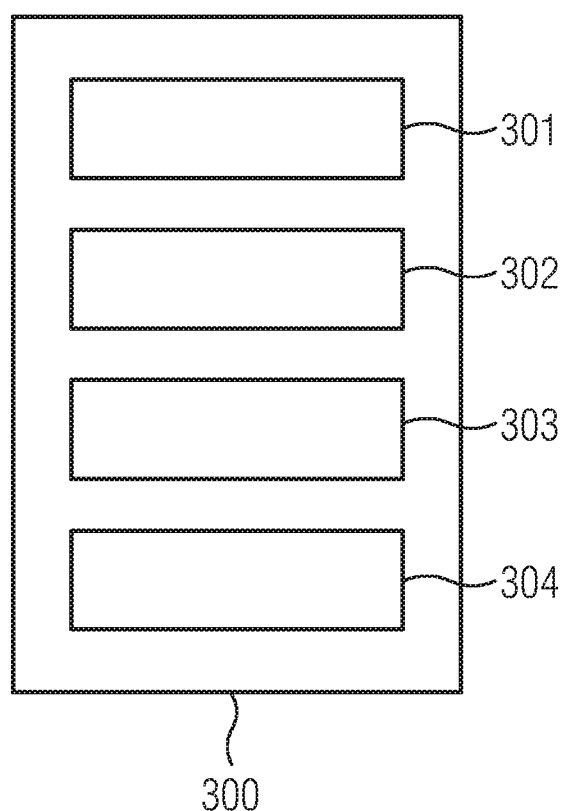
FIG. 3 shows a providing apparatus.

FIG. 3 displays a providing apparatus 300 for providing a normalized image. The displayed providing apparatus 300 is embodied to execute a method according to the invention. The providing apparatus 300 comprises an interface 301, a calculation unit 302, a memory unit 303 and a input and/or output unit 304.

In particular, the providing apparatus can be a computer, a microcontroller, or an integrated circuit. As an alternative, the providing apparatus 300 can be a real or a virtual group of computers (the technical term for a real group of computers is "cluster", the technical term for a virtual group of computers is "cloud").

An interface 301 can be embodies as a hardware interface or as a software interface (e.g. PCI-Bus, USB or Firewire). A calculation unit 302 can comprise hardware elements and software elements, for example a microprocessor or a field programmable gate array. A memory unit 303 can be embodied as non-permanent main memory (e.g. random access memory) or as permanent mass storage (e.g. hard disk, USB stick, SD card, solid state disk). A input and/or output unit 404 comprises at least one input unit (e.g. mouse, keyboard) and/or at least one output unit (e.g. display, printer).

Figure 4:
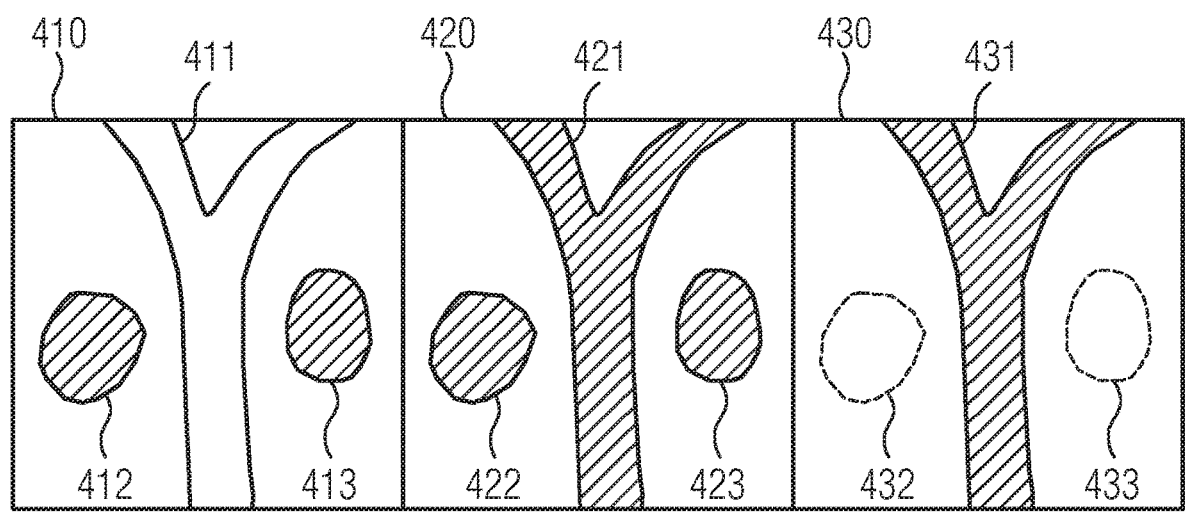
FIG. 4 shows a first image, a second image and a subtraction of the first and the second image, each comprising a vessel, without motion artifacts.

FIG. 4 shows a first image 410, a second image 420 and a subtraction image 430, wherein the subtraction image 430 is calculated as the difference between the first image 410 and the second image 420. Each of the images 410, 420, 430 comprises a vessel 411, 421, 431 and other image regions 412, 413, 422, 423, 432, 433.

The field of view of the first image 410 equals the field of view of the second image 420, and there was no motion of the field of view between the recording time of the first image 410 and the second image 420, so there is no motion artifact in the subtraction image 430.

The vessel 411 in the first image 410 is filled with blood, the vessel 421 in the second image 420 is additionally filled with a contrast liquid, so that the X-ray attenuation is higher than in the first image 410, so that the X-ray intensity is lower in the second image 420 than in the first image 410. As a result, in the subtraction image 430 the vessel is displayed with a negative intensity.

The X-ray attenuations of the other regions 412, 413 in the first image 410 equals the X-ray attenuation of the other regions 422, 423 in the second image 420, so that the X-ray intensities are equal in the first image 410 and in the second image 420. As a result, the intensity of the other regions 432, 433 in the subtraction image 430 is zero up to noise.

Figure 5:
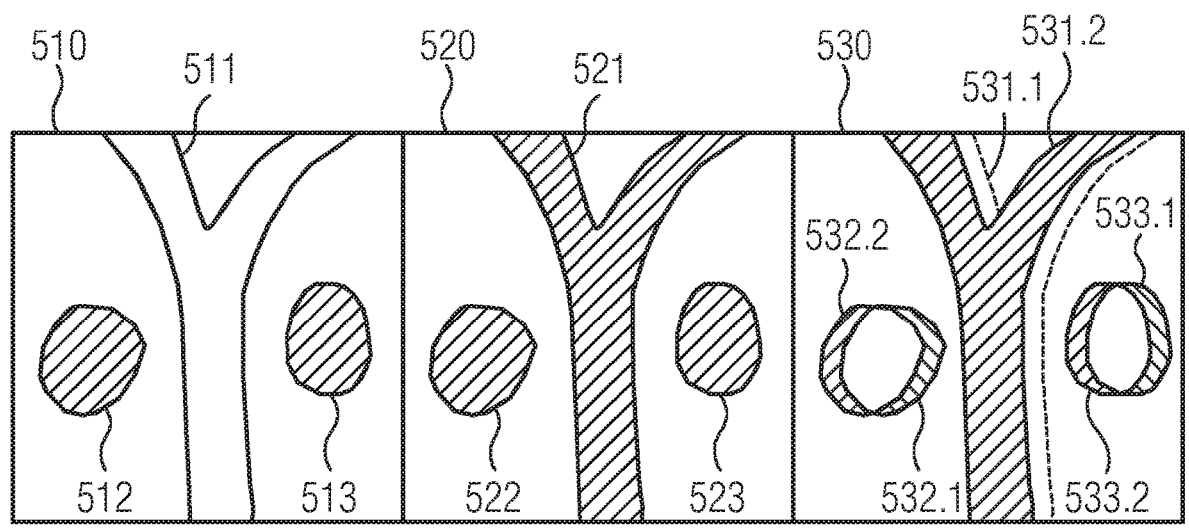
FIG. 5 shows a first image, a second image and a subtraction of the first and the second image, each comprising a vessel, with motion artifact.

FIG. 5 shows a first image 510, a second image 520 and a subtraction image 530, wherein the subtraction image 530 is calculated as the difference between the first image 510 and the second image 520. The first image 510 and the second image 520 comprise a vessel 511, 521 and other image regions 512, 513, 522, 523.

The vessel 511 in the first image 510 is filled with blood, the vessel 521 in the second image 520 is additionally filled with a contrast liquid, so that the X-ray attenuation is higher than in the first image 510, so that the X-ray intensity is lower in the second image 520 than in the first image 510.

The X-ray attenuations of the other regions 512, 513 in the first image 510 equals the X-ray attenuation of the other regions 522, 523 in the second image 520, so that the X-ray intensities are equal in the first image 510 and in the second image 520.

In comparison with the first image 510, the field of view of the second image 520 is shifted to the left. This shift can be caused by a motion within the field of view (e.g. by the breathing of a patient), or by a motion of the X-ray imaging system. As a consequence, one can find motion artifacts in the subtraction image 530. For orientation, in the subtraction image 530 the vessel 531.1 in the position of the first image 510 and the vessel 531.2 in the position of the second image 520 are displayed. If one assumes that the vessel 511 in the first image 510 is characterized by the same X-ray attenuation as its surrounding, this results in no motion artifact in the subtraction image 530, only the vessel 531.2 in the position 520 second image 520 is visible (with negative intensity).

In contrast, motion artifacts can be found if considering the other regions 512, 513, 522, 523. In the subtraction image 530, the position of the other regions 532.1, 533.2 in the first image 510 and the position of the other regions 532.2, 533.2 in the second image 520 is displayed. Since the first image 510 and the second image 520 contribute to the subtraction image 530 with different signs, in the subtraction image 530 one finds as a motion artifact areas with positive intensity and areas with negative intensity, wherein the corresponding areas have the same size. In FIG. 5, positive intensity is displayed by a hatching from the upper left to the lower right, and negative intensity is displayed by a hatching from the upper right to the lower left.

In the following figures the non-normalized intensities 601 and the normalized intensities 801 are displayed as an axis corresponding to an independent variable. Despite this presentation the terms "normalized intensities" 801 and "non-normalized intensities" 601 may refer to multisets, i.e. sets where elements can more than once. For example, if in the non-normalized image there are several pixels characterized by the same non-normalized intensity, this said non-normalized intensity is contained in the non-normalized intensities 601 more than once. In other words, the non-normalized intensities 601 and the normalized intensities 801 can refer to a tuple without ordering.

In the formulas above, in particular "normalized intensities" and "non-normalized intensities" have to be understood as axes corresponding to an independent variable if the notion with an integral is used (e.g. in the calculation of the measured mean and the measured deviation). If otherwise the notion with a sum is used, "normalized intensities" and "non-normalized intensities" have to be understood as multisets. In particular, "normalized intensities" and "non-normalized intensities" have to be understood as multisets if the relation between the normalized intensities of the second pixels and the non-normalized intensities of the first pixels is described.

Figure 6:
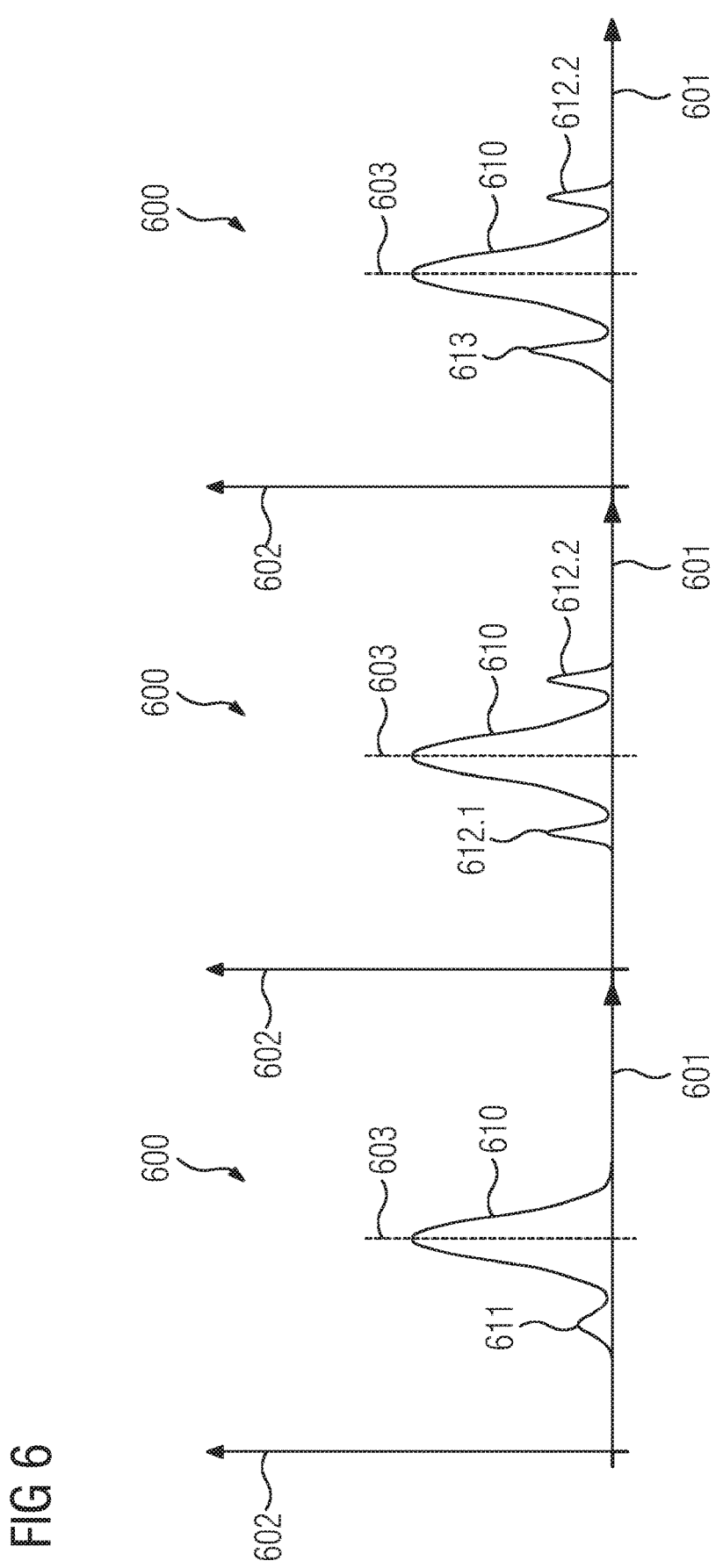
FIG. 6 shows plain histograms of subtraction images.

FIG. 6 shows examples of plain histograms 600 of intensities for subtraction images 430, 530 without motion artifacts, but with contrast fluid (left), for subtraction images 430, 530 with motion artifacts, but without contrast fluid (middle), and for subtraction images 430, 530 with motion artifacts and contrast fluid (right).

The plain histogram 600 is a map from non-normalized intensities 601 to their relative frequency 602 in the subtraction image 430, 530. The dashed line indicates the origin 603 of the non-normalized intensities 601. In other words, the origin 603 is the non-normalized intensity with value zero.

The plain histogram 600 comprises a noise peak 610, which is due to image noise in the first image 410, 510 and/or the second image 420, 520, and which is symmetric with respect to the origin 603 in a good approximation. The plain histogram 600 can furthermore comprise a contrast peak 611, which is due to vessels being filled with contrast fluid in the second image 420, 520, but not in the first image 410, 510, as explained within the description of FIG. 4 and FIG. 5. The plain histogram 600 can furthermore comprise motion artifact peaks 612.1, 612.2. If there is no contrast fluid involved, the motion artifact peaks 612.1 and 612.2 are symmetric with respect to the origin 603 up to boundary effects, as explained in the description of FIG. 5. If motion artifacts and contrast fluid is involved, the motion artifact peak 612.1 and the contrast peak 611 are merge to a total peak 613.

Figure 7:
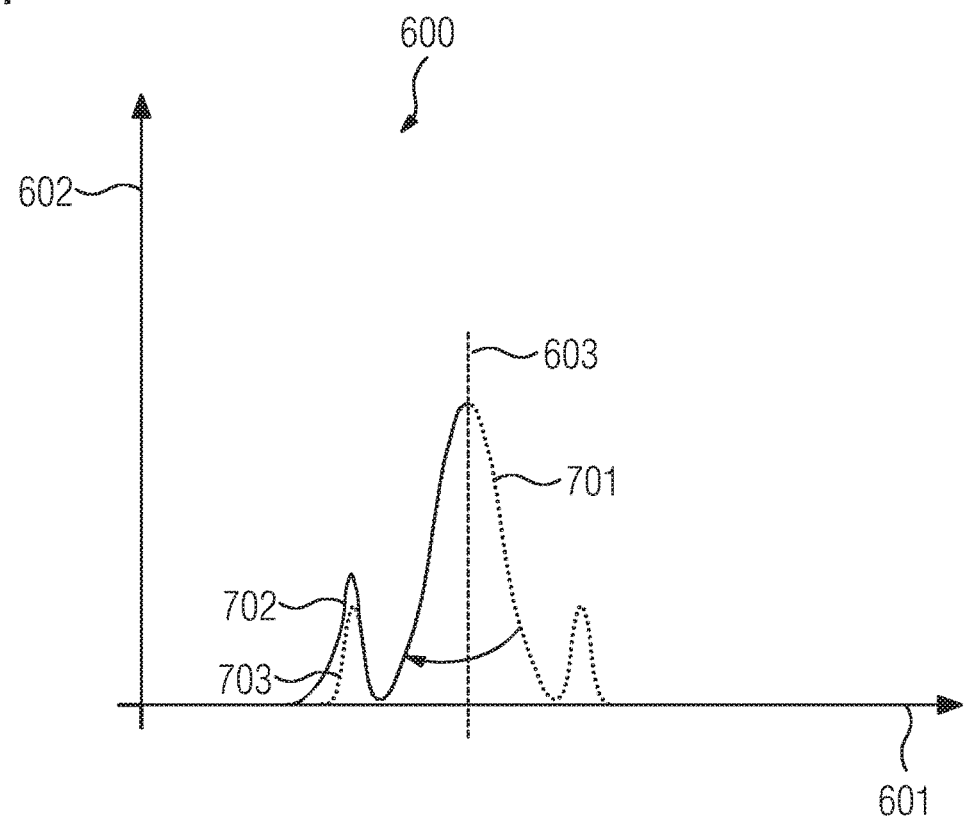
FIG. 7 shows a calculation method for the subtraction histogram.
Figure 8:
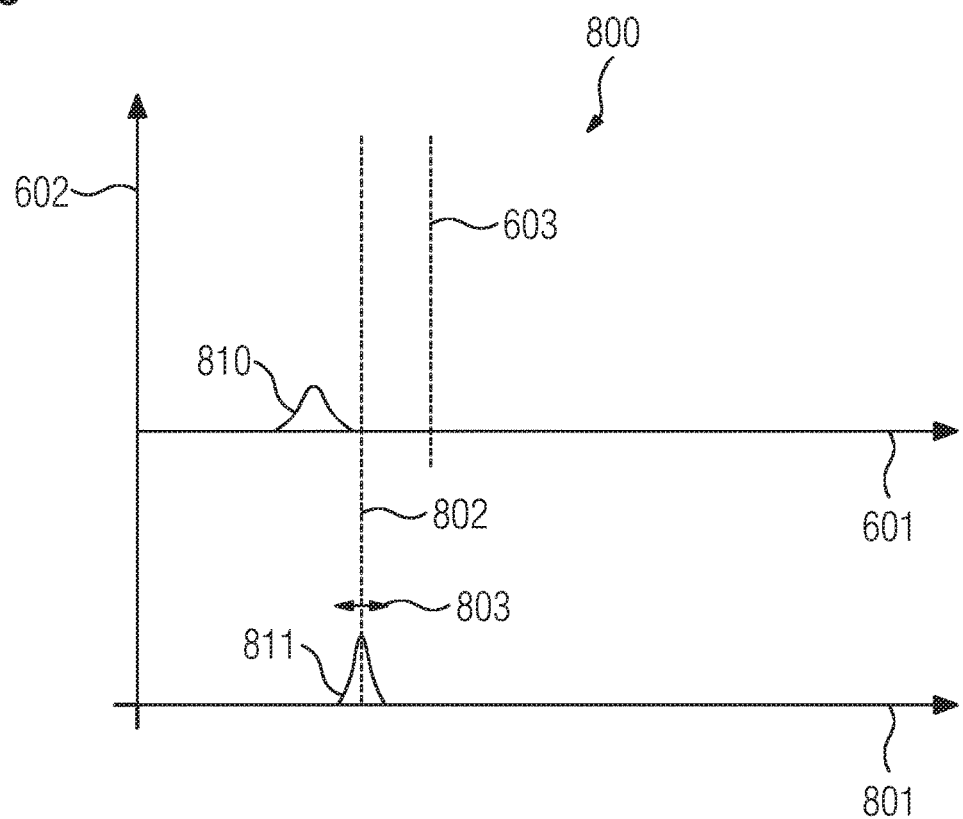
FIG. 8 shows a subtraction histogram.

FIG. 7 displays the method of calculating a subtraction histogram 800 from a plain histogram 600, the resulting subtraction histogram 800 is displayed in FIG. 8. The plain histogram 600 is divided in a positive part 701, which is the plain histogram 600 restricted to positive non-normalized intensities 601, and a negative part 702, which is restricted to negative non-normalized intensities 601. The positive part 701 can be mirrored with respect to the origin 603, resulting in a mirrored positive part 703. The resulting subtraction histogram 800 can then be interpreted as the difference of the negative part 702 and the mirrored positive part 703, restricted to negative non-normalized intensities 601.

The subtraction histogram 800 is displayed with the non-normalized intensities 601 and with the normalized intensities 801 as independent variable. The curve 810 is the difference between the mirrored positive part 703 and the negative part 802 with respect to the non-normalized intensities 601; the curve 811 is the difference between the mirrored positive part 703 and the negative part 802 with respect to the normalized intensities 801. Both curves 810, 811 can be interpreted as histograms.

The normalized intensities 801 are calculated from the non-normalized intensities 601 by applying a linear transformation as described above, so that the mean of the histogram 811 corresponds to a reference mean 802, and so that the standard deviation of the histogram 811 corresponds to a reference deviation 803.

Figure 9:
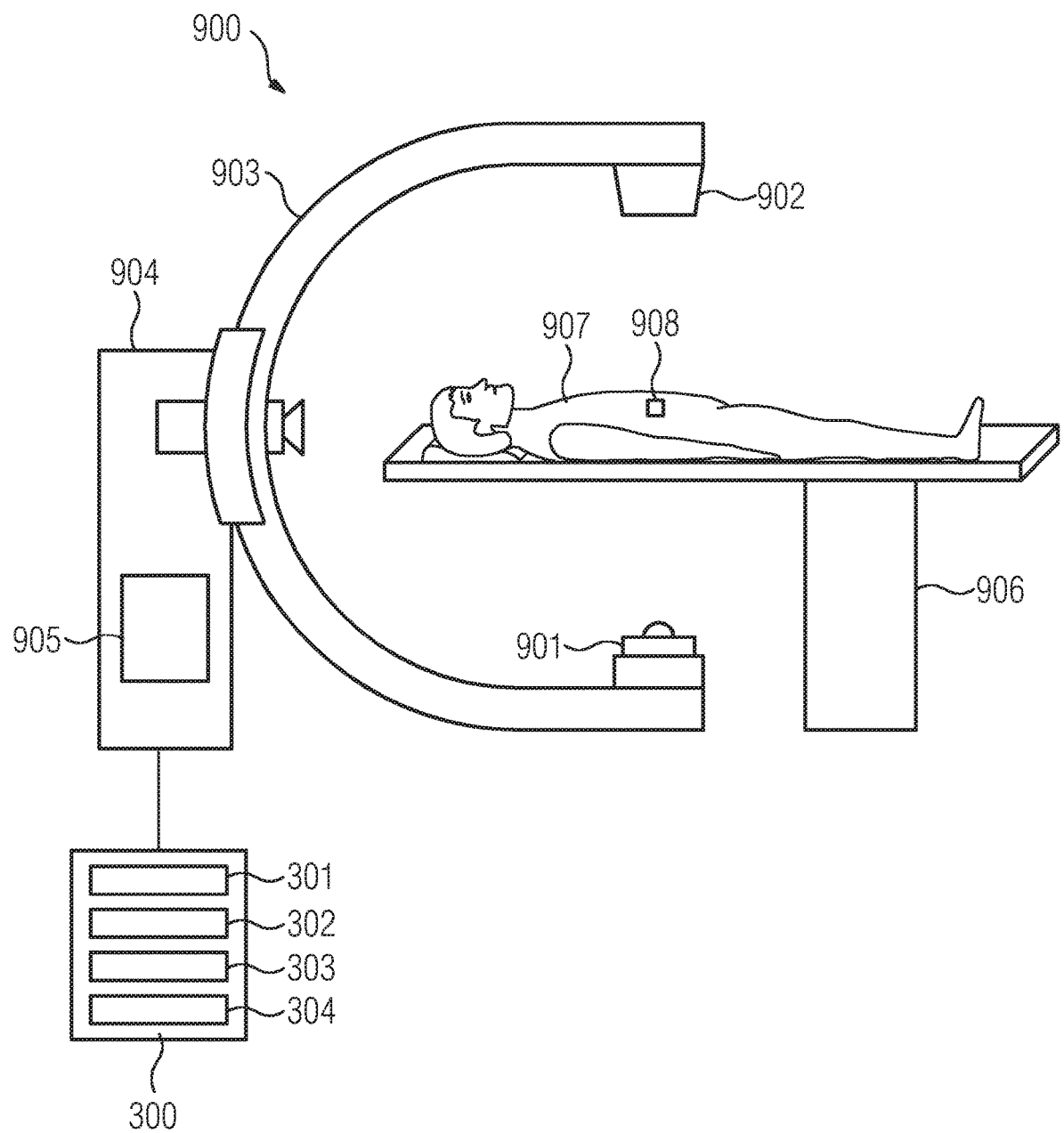
FIG. 9 shows a C-arm X-ray imaging unit.

FIG. 9 displays an X-ray imaging device 900 which is connected to a providing apparatus 300. In the displayed embodiment the X-ray imaging device 900 is a C-arm X-ray imaging device. The X-ray imaging device 900 comprises a X-ray source 901 for generating X-rays and a X-ray detector 902 for receiving X-rays. The X-ray source 901 and the X-ray detector 902 are embodied at opposite sides of a C-arm 903. The C-arm 903 of the X-ray imaging device 900 is attached to a stand 904. The stand 904 comprises devices (e.g. motors) for changing the position of the C-arm 903, in particular, the C-arm can be rotated around two different axis. Furthermore, the X-ray imaging device 900 comprises a control and analyzing unit 905 as well as a patient positioning unit 906, which can be used for positioning a patient 907. Using the control and analyzing unit 905 the position of the C-arm 903 can be adjusted, and the C-arm 803 can be rotated around the patient 907. Furthermore, using the control and analyzing unit 905 two-dimensional X-ray projections of the patient can be recorded. In general it is possible to record higher-dimensional data by combining two or more two-dimensional X-ray projections. As an alternative to the displayed embodiment, the control and analyzing unit 905 can comprise the providing apparatus 300.

In this embodiment the X-ray source 901 is an X-ray tube. Alternatively, the X-ray source 901 can also be a linear accelerator, an X-ray laser, an synchrotron or a cyclotron. Furthermore, in this embodiment the X-ray detector 902 is a flat panel X-ray detector. Alternatively, the X-ray detector 902 can be a semiconductor detector, an X-ray film, a photostimulable phosphor plate, or an X-ray image intensifier.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing a normalized image, the method comprising:
  receiving a non-normalized image including first pixels and non-normalized intensities, each of the first pixels being characterized by one of the non-normalized intensities;
  determining a subtraction histogram, the subtraction histogram being configured to map a first intensity to a difference between a relative frequency of the first intensity and a relative frequency of a second intensity, the first intensity being one of the non-normalized intensities and the second intensity being one of the non-normalized intensities; and providing the normalized image based on the non-normalized image and the subtraction histogram, the normalized image including second pixels and normalized intensities, and each of the second pixels being characterized by one of the normalized intensities.

2. The method of claim 1, wherein a relative deviation between a negative of the first intensity and the second intensity is less than 0.5.

3. The method of claim 2, wherein the relative deviation between the negative of the first intensity and the second intensity is less than 0.1.

4. The method of claim 3, wherein the relative deviation between the negative of the first intensity and the second intensity is less than 0.01.

5. The method of claim 2, wherein each of the second pixels is assigned to one of the first pixels, and wherein the normalized intensities, pixel by pixel, depend on the non-normalized intensities.

6. The method of claim 1, wherein the second intensity is a negative of the first intensity.

7. The method of claim 6, wherein each of the second pixels is assigned to one of the first pixels, and wherein the normalized intensities, pixel by pixel, depend on the non-normalized intensities.

8. The method of claim 1, wherein the subtraction histogram is configured to map the first intensity to zero in response to the first intensity being positive.

9. The method of claim 1, wherein each of the second pixels is assigned to one of the first pixels, and wherein the normalized intensities, pixel by pixel, depend on the non-normalized intensities.

10. The method of claim 9, wherein
a normalized intensity of one of the second pixels is a linear function of a non-normalized intensity of the one of the first pixels, and
the one of the second pixels is assigned to the one of the first pixels.

11. The method of claim 9, wherein
the receiving includes receiving a reference mean and a reference deviation, and
the providing is based on the reference mean and the reference deviation.

12. The method of claim 11, wherein each of the second pixels is assigned to one of the first pixels, wherein a normalized intensity value of one of the second pixels is calculated as a sum of two numbers, wherein a first of the two numbers is a product of a first constant and a non-normalized intensity value of the one of the first pixels assigned to the one of the second pixels, wherein a second of the two numbers is a second constant, wherein the first constant is a ratio of the reference deviation and a measured deviation, and wherein the second constant is the reference mean subtracted by a product of the first constant and a measured mean of the subtraction histogram.

13. The method of claim 1, wherein
the providing is based on a measured mean and a measured deviation,
the measured mean is a mean of the subtraction histogram, and
the measured deviation is a standard deviation of the subtraction histogram.

14. The method of claim 1, wherein the determining a subtraction histogram comprises:
determining a plain histogram, the plain histogram being configured to map the first intensity to the relative frequency of the first intensity, and
determining the subtraction histogram based on the plain histogram.

15. A non-transitory computer program product comprising a computer program, the computer program being loadable into a memory of an apparatus and including program code sections configured to cause the apparatus execute the method of claim 1 when the computer program is executed in the apparatus.

16. A non-transitory computer-readable medium, storing program code sections of a computer program, the program code sections being at least one of loadable into or executable by an apparatus, and being configured to cause the apparatus to execute the method of claim 1 when the program code sections are executed in the apparatus.

17. An apparatus, comprising:
at least one processor configured to cause the apparatus to
receive a non-normalized image including first pixels and non-normalized intensities, each of the first pixels being characterized by one of the non-normalized intensities,
determine a subtraction histogram, the subtraction histogram being configured to map a first intensity to a difference between a relative frequency of the first intensity and a relative frequency of a second intensity, the first intensity being one of the non-normalized intensities and the second intensity being one of the non-normalized intensities, and
provide a normalized image based on the non-normalized image and the subtraction histogram, the normalized image including second pixels and normalized intensities, and each of the second pixels being characterized by one of the normalized intensities.

18. The apparatus of claim 17, wherein a relative deviation between a negative of the first intensity and the second intensity is less than 0.5.

19. An X-ray imaging device comprising the apparatus of claim 18.

20. An X-ray imaging device comprising the apparatus of claim 17.

21. The apparatus of claim 17, wherein the second intensity is a negative of the first intensity.

22. The apparatus of claim 17, wherein the subtraction histogram is configured to map the first intensity to zero in response to the first intensity being positive.

23. The apparatus of claim 17, wherein each of the second pixels is assigned to one of the first pixels, and wherein the normalized intensities, pixel by pixel, depend on the non-normalized intensities.

24. The apparatus of claim 23, wherein
a normalized intensity of one of the second pixels is a linear function of a non-normalized intensity of the one of the first pixels, and
the one of the second pixels is assigned to the one of the first pixels.

\* \* \* \* \*